United States Patent [19]

Tsaprazis

[11] Patent Number: 4,731,578
[45] Date of Patent: Mar. 15, 1988

[54] ELECTRICAL SENSING SYSTEM FOR MEASURING FERROUS PARTICLES WITHIN A FLUID

[75] Inventor: Edward Tsaprazis, Havertown, Pa.

[73] Assignee: Aeroquip Corporation, Jackson, Mich.

[21] Appl. No.: 729,759

[22] Filed: May 2, 1985

[51] Int. Cl.$^4$ .................. G01N 27/74; G01R 33/12
[52] U.S. Cl. .................. 324/204; 324/225; 324/234; 324/236; 340/631
[58] Field of Search ............ 324/204, 225, 228, 234, 324/236, 237, 238, 327, 59; 73/64; 340/631; 361/180

[56] References Cited

U.S. PATENT DOCUMENTS

| | | | |
|---|---|---|---|
| 2,721,994 | 10/1955 | Brown | 324/236 X |
| 3,378,763 | 4/1968 | Hastings | 324/225 X |
| 4,130,792 | 12/1978 | Sullivan | 324/236 X |
| 4,219,805 | 8/1980 | Magee et al. | 324/204 X |
| 4,519,696 | 5/1985 | Bruyndonckx et al. | 324/204 X |

FOREIGN PATENT DOCUMENTS

| | | | |
|---|---|---|---|
| 1505716 | 11/1967 | France | 324/236 |
| 681365 | 8/1979 | U.S.S.R. | 324/225 |

OTHER PUBLICATIONS

Ogren, V. G., Sensor Circuit Utilizing Variable Inductance Input, IBM Tech. Discl. Bull., vol. 14, No. 4, Sep. 1971, p. 1220.

Primary Examiner—Gerard R. Strecker
Attorney, Agent, or Firm—Lipton & Famiglio

[57] ABSTRACT

This invention relates to a device for detecting electrically inductive particles in a fluid medium and is of particular use for detecting ferrous particles in the lubricant of an engine or mechanical transmissions thereby giving warning of malfunction of the engine or the transmission. The invention is of particular importance for the operation of an internal combustion engine, especially highly stressed helicopter and aircraft engines wherein prior warning of a malfunction permits corrective action prior to a catastrophic failure.

1 Claim, 5 Drawing Figures

ELECTRICAL SENSING SYSTEM FOR MEASURING FERROUS PARTICLES WITHIN A FLUID

Field of the Invention.

Metal parts in an internal combustion engine or mechanical transmissions, e.g., gear boxes, undergo wear because of friction between the metallic parts or a metal part and nonmetallic part. The result of the wearing friction is metallic contamination of the lubricating or transmission fluid. The contamination comprises metal particles of many sizes and shapes. Monitoring of the metal particles contained in the fluid can provide early warning of the deterioration of a mechanical device, e.g. the internal combustion engine.

Description of the Prior Art.

U.S. Pat. No. 4,323,843 discloses an apparatus for detecting magnetisible electrically conductive particles in a fluid medium using two spaced apart electrodes electrically insulated one from the other. The conductive particles are attracted to the flux which forms between the two electrodes, and participates in the bridge which forms between the two electrodes, and therefore effect the electrical inductivity of the bridge which then can provide a correlation with the concentration of the conductive particles in the fluid.

U.S. Pat. No. 3,502,970 discloses a system for detecting metal particles in an engine lubricating system. In this system a capacitance probe detects accumulation of metal particles on one side of a filter screen while a dummy probe is provided on the downstream side of the filter to compensate for changes in the lubricating fluid. The capacitance probe and dummy probe are connected in an RF bridge, the output of which is indicated on a meter. Unbalance of the bridge causes a reading on the meter indicating particular accumulation.

U S. Pat. No. 4,008,464 discloses an apparatus for providing an electrical warning signal when ferrous contamination builds up in the lubricant of a geared lubricated mechanism. The apparatus comprises first and second magnetic members and means for fixedly positioning the magnetic members within the housing of the mechanism, exposed to the normal lubricant flow. Means are provided so that when ferrous contamination on one of the magnet members comes into contact with ferrous contamination on the other magnetic member, the circuit is closed and a warning signal is provided to the operator of the mechanism.

U.S. Pat. No. 4,127,808 discloses a transistorized engine chip detection system which includes a milliammeter to give a visual indication of chip buildup and a full light to operate at a critical preset level, using a voltage divider network, a decrease in the resistance in the chip detector will cause an increase in the current flow, and subsequent lighting of a warning light.

U.S. Patent No. 2,349,992 discloses an electrical circuit designed so that variations of its capacity or resistance, produced by contamination in oil, are measured. Involved is a measuring chamber designed in the manner of a filter with probe elements sensitive to the contaminations in the oil, is inserted in the oil circulation system and its operating conditions are electrically observed and indicated.

U.S. Pat. No. 4,219,805 discloses the use of magnetic attraction to capture ferrous particles circulating in lubricating systems. The captured particles are used to actuate the generation of a signal pulse on capture, the amplitude and decay characteristics of which are essentially proportional to the mass of the individual particles trapped. The signal pulses, after discrimination by suitable logic circuitry are converted to both analog and digital values.

U.S. Pat. No. 3,238,452 discloses means for tracing fine particulate solids and undissolved water in fuels, e.g., jet fuel. Involved is the diversion of a side stream of the fuel flowing through a line and conducting it through a filter-capacitive-measuring cell, and then through a second, downstream from the first cell, a second capacitive-measuring cell connected in series with the filter cell. Both cells are capacitors with plates of each being connected through a selector switch to a Wheatsone bridge circuit. Comparison of the capacitive reactance of the cells and that of a standard capacitor measures the solid content and water in the fuel.

U.S. Pat. No. 3,078,709 involves developing an electrical signal via the impingment upon of a grid of electrically conductive material, by flow irregularities such as gas bubbles.

U.S. Pat. No. 4,070,660 discloses a wear particle detector which discriminates between large and smaller particles.

SUMMARY OF THE INVENTION

The present invention, like those of the prior art, uses magnetic attraction to capture ferrous particles circulating in the system. An inductance coil situated around a permanent magnet is used as a probe for insertion into an oil gearbox for the metering of metallic debris therein. As ferrous particles are captured on the permanent magnet containing the sensor probe, the electric inductance of the probe is thereby changed due to the proximity of the various particles to the coil. This change in inductance is used to change the operating frequency of an electrical bandpass filter.

A fixed frequency oscillator having a known, stable frequency output is used to drive the filter at its center frequency, which is the frequency in the center of its bandpass when there have been no particle buildup. As the filter changes frequency, the output voltage of the filter is changed thereby creating an output of the filter whose amplitude is proportional to the mass of various particle buildup.

In the preferred embodiment, two coils are utilized in the sensor to compensate for temperature variation in the gear oil. The circuit disclosed herein shows a method of amplifying and metering the output of the filter to provide a signal for display on an analog or digital indicator.

It is therefore a principal object of the present invention to provide a ferrous particle capturing device for use in circulating liquid systems wherein the mass of the total accumulated particles so captured are measured. It is a further object of the present invention to provide signals suitable for analog or digital display, the amplitudes of which are a function of the mass accumulated on the particle capturing device for the estimation of the amount of material accumulated. Other and further objects of this invention will become apparent to those skilled in the art upon consideration of the following specification when read in conjunction with the attached drawings.

DESCRIPTION OF THE PREFERRED EMBODIMENT

Figure 1:
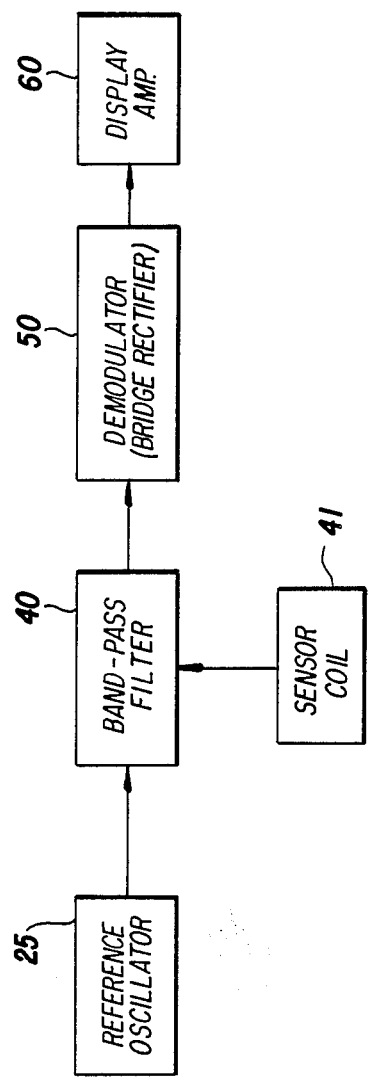
FIG. 1 is a block diagram of a debris monitoring system according to the present invention, showing the basic circuit used in the present design.

Referring now to FIG. 1, a block diagram of the overall system is shown. This block diagram shows the basic components of the present invention including a reference oscillator 25, a bandpass filter 40, a demodulator circuit 50 and a display amplifier 60. Sensor coil 41 is shown in FIG. 1 as a separate component, although in reality it is an integral part of the bandpass filter 40 as will be explained in the electrical schematic diagram. Reference oscillator 25 is used to generate a fixed known single frequency output, having a constant voltage value of the sine-wave output. It will be appreciated that the actual value of the voltage output would vary according to design and the set value used in a particular design and application. In the preferred embodiment, voltage output peak to peak values 5 volts to 20 volts are used with good results. The constant amplitude sine-wave output of reference oscillator 25 is filtered through bandpass filter 40. Bandpass filter 40 has a known frequency curve and frequency to amplitude output. Sensor coil 41 is an integral part of the feedback loop in bandpass filter 40 and it will be appreciated that the frequency response of bandpass filter 40 can be changed by the variance of the inductance coil, used as its frequency determining element. The output of bandpass filter 40 is transmitted to demodulator 50, which is a diode bridge rectifier used to change the AC output of the bandpass filter to a DC value which is proportional to the peak to peak amplitude output of bandpass filter 40. After demodulation by the bridge rectifier circuit, the value of the remaining DC signal is used to drive a display amplifier which can be used to deflect an analog metering instrument or digital display, as may be necessary in the particular application of the present invention.

In a variation of the preferred embodiment, the sensor coil 41 is actually comprised of two separate coils within the feedback and input circuit design in bandpass filter 40 which will be described in more detail below. By utilizing two coils, it is possible to compensate for temperature changes or differentials between the inductance and/or resistance of the first coil at a resting temperature and the inductance and/or resistance of the first coil when the circulating fluid temperature rises.

Figure 2:
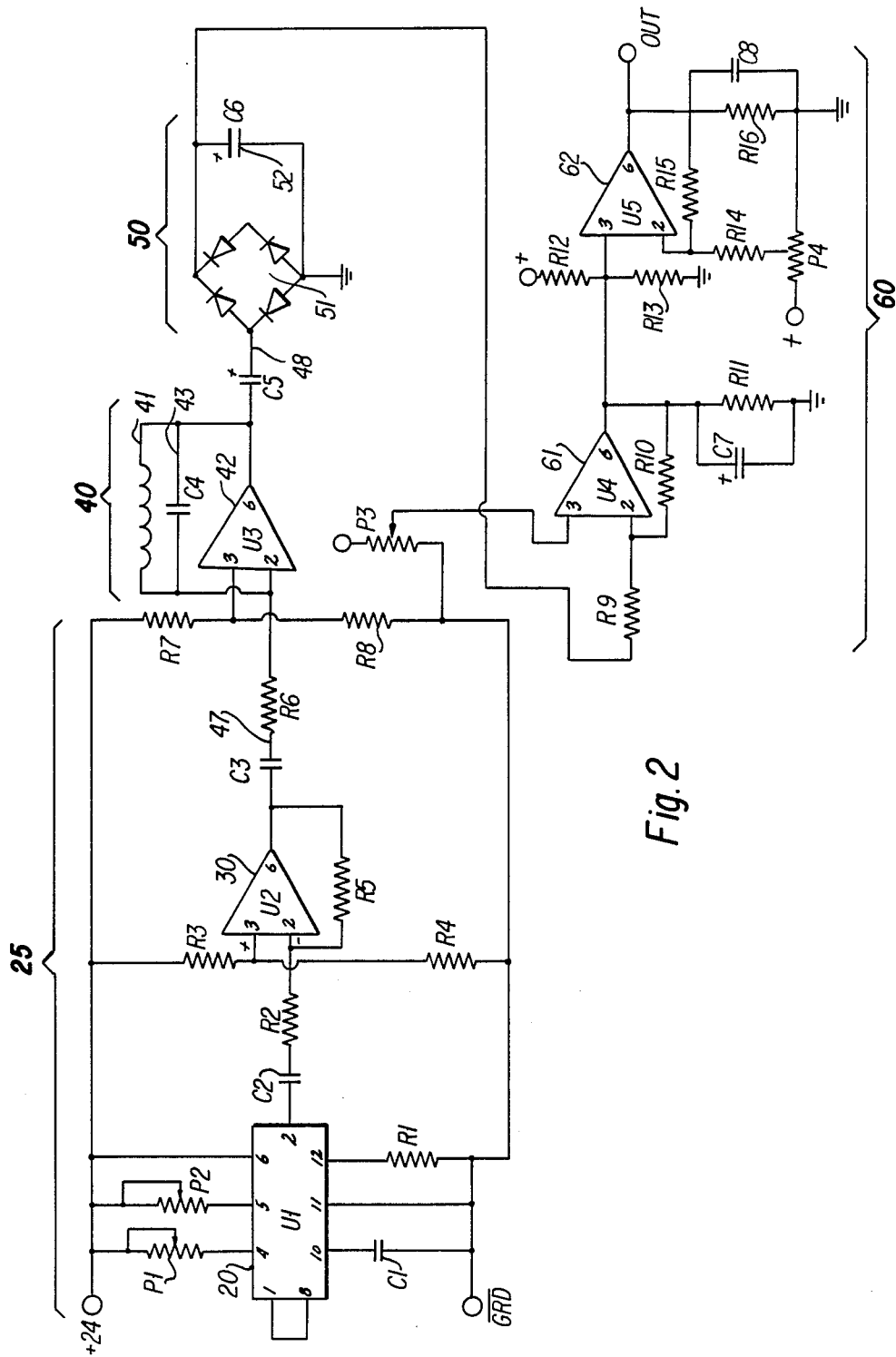
FIG. 2 is an electrical schematic diagram showing the basic concept of the debris monitoring system.

Turning now to FIG. 2, the present invention will be described in accordance with the electronic schematic diagram set forth so that the details of design may be appreciated. The reference oscillator is centered about an integrated circuit chip 20, which is a design well know to those skilled in the art. It is possible to design a sine-wave generator or oscillator about a single integrated circuit which requires only a few external peripheral components for it to operate at a given frequency. In the present invention, the integrated circuit chip utilized is a 8038 though a large variety of integrated circuit chips exist which may be used. It will be appreciated that all of the electrical components within the present design will operate at 24 volts in that the contemplated use for the invention is aircraft and specifically helicopters, the most common electrical system of which is 24 volts. Therefore, the present circuits are designed to operate without further voltage conversion. However, the same circuit design could be developed for use with a 12 volt source utilizing components designed for such.

Integrated circuit oscillator chip 20 may operate at a frequency of 20 to 200 kilohertz. The actual operating frequency depends on the set point of peripheral components utilized in the operation of the present integrated circuit. FIG. 2 will show the placement of various electrical components, specifically resistors and capacitors utilized in operation of integrated circuit chip 20, along with its pin numbers. The output of the integrated circuit 20 is fed through pin 2 of chip 20 to amplifier 30, through C2, shown on the schematic. It will be appreciated that the design of amplifier 30 is an operational amplifier, the gain of which can be carefully controlled by the selection of peripheral components, specifically the value of R5 with reference to R2. Operational amplifier 30 serves to amplify the output of the reference oscillator 20 to a given and fixed value of peak to peak voltage, as well as isolating the output of chip 20 from any influences due to circuit loading by the components in FIG. 2. The output of amplifier 30 is fed through resistor R6 to the input of operational amplifier 42, which is central to the operation of the bandpass filter 40. Amplifier chip 42 has an inductance coil 41 and a capacitor 43, in parallel to each other, and across its output to its inverting input as shown in FIG. 2. This has the effect of causing operational amplifier 42 to operate as a bandpass filter, being two-pole in design and having a center frequency which is controlled by the actual inductance of probe 41 and the value of capacitor 43. Probe 41 and capacitor 43 form a parellel resonant circuit which sets the center frequency of filter 40. The design of the bandpass filter 40 will be well known to those skilled in the art and it will be appreciated that in other types of filter designs using operational amplifiers such as 42 may be utilized using similar components for the purposes of designing a two-pole frequency filter with a known frequency vs. amplitude response characteristic. The output of bandpass filter 40, is fed through C5 to the demodulator circuit 50, which is primarily a wheatstone bridge rectifier 51. The output of rectifier 51 is fed to capacitor 52 which is used to smooth the output, and the resulting DC signal is fed to the input of operational amplifier 61, through R9. The output of operational amplifier 61 is fed to the input of operational amplifier 62, the output of which is used to drive an analog meter or a digital display. It will be appreciated that amplifier 61 and 62 are utilized in a conventional fashion to provide a known value of amplification from the output of the demodulator 50.

Central to the operation of the present invention is the placement of coil 41, which is the coil used in the probe to be placed in close proximity to the circulating fluid.

Figure 4:
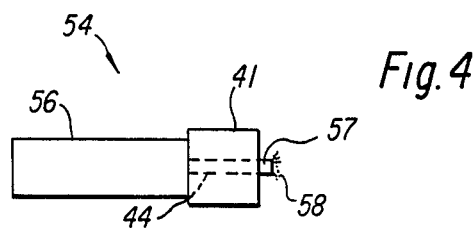
FIG. 4 is a view of a type of sensor head to be used in the present invention.

Coil 41 is an integral part of sensor 54, shown in FIG. 4. As sensor 54 is shown, it consists essentially of a cylindrical permanent magnet 56 set concentrically into the coil 41 which is an inductance coil. This coil is fitted over a pole piece of the magnet which extends through the axial position of the coil 41 as shown in FIG. 4. Coil 41 is a coil of wire wound about a pole piece 57 of magnet 56 using conventional techniques for winding coils about any cylindrical object. Pole piece 57 is attached to magnet 56 as the axis of magnet 56, shown for clarity at 44, and extends beyond the magnet 56 as shown in FIG. 4. Magnet 56 terminates at the interface of coil 41 and magnet 56. Pole piece 57 is attached to the end of magnet 56 at the same interface. In the arrangement shown, the lines of flux produced by magnet 56 create an attractive magnetic zone in the vicinity of the collection surface of the pole piece 57. When a ferrous particle enters the magnetic zone and is captured on the surface of 57, it will be appreciated that it would change the inductance value of coil 41. Since coil 41 is operatively connected, through leads (not shown), to the bandpass filter as shown in FIG. 2, it should be appreciated that as ferrous material accumulates on the face of piece 57, the feedback impedance of the oscillator is changing in proportion to the accumulated debris. This would occur because there is a relationship between the mass of the debris accumulated on the surface of 57 and the change of impedance of coil 41 that this mass accumulation creates.

Therefore, in the operation of the total system, the center frequency of bandpass filter 40 changes as the inductance of coil 41 changes due to the accumulation of ferrous matter on pole piece 57. With this change of center frequency of filter 40, filter 40's transfer function changes to the extent that the voltage amplitude present at point 48 in FIG. 2, decreases as the mass on pole piece 57 increases.

In the operation of the system, the starting frequency of filter 40, being its center bandpass frequency without the accumulation of mass on 57, should be matched to the output frequency of reference oscillator circuit 25. In this way, any accumulation of debris will cause a shift of the center frequency of filter 40, thereby causing an amplitude decrease irrespective of whether the bandpass filter frequency has been shifted upwards or downwards in center frequency.

Figure 3:
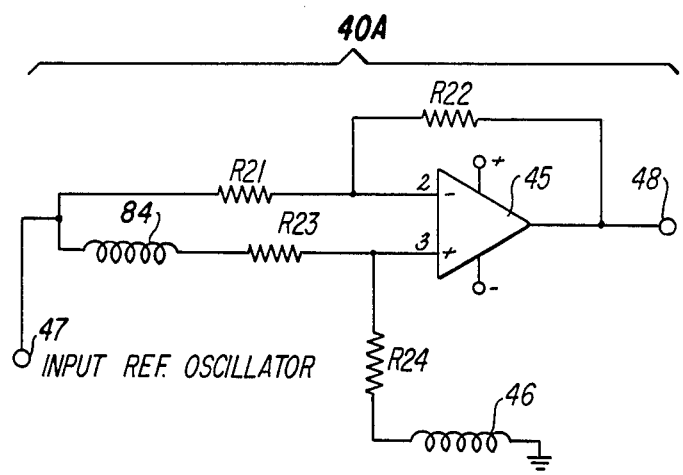
FIG. 3 is a preferred embodiment of the present monitoring system showing the temperature compensating coils.

In the operation of the present invention, it will be appreciated that it is desirable that the only parameter which changes the inductance of coil 41 would be the accumulation of debris 58 on pole piece 57. However, it is possible that the inductance value of coil 41 would change with the temperature of any fluid in the proximity of coil 41. This occurs when the temperature of the coil is increased or decreased from its calibration temperature. It is possible to eliminate this undesirable characteristic by the substitution of the circuit shown in FIG. 3, which is a variation of bandpass filter 40 shown in FIG. 2. Bandpass filter 40A shown in FIG. 3 can be applied in the entire circuit shown in FIG. 2 by the substitution of filter 40 A for filter 40 shown in FIG. 2. The substitution would occur by matching the input circuit 47 in FIG. 3 with point 47 on FIG. 2. Likewise, the output of filter 40A at 48 in FIG. 3 can be connected at point 48 in FIG. 2. In essence, the new bandpass filter design shown in FIG. 3 is simply substituted for the bandpass filter designs shown in FIG. 2 at 40.

Figure 5:
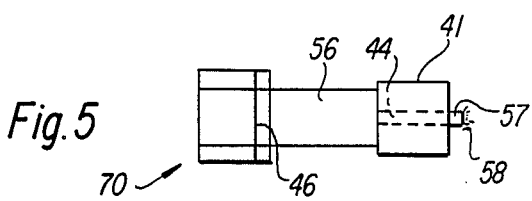
FIG. 5 is a view of a type of sensor head to be used with the schematic diagram of preferred embodiment shown in FIG. 3 of the present invention.

Returning to FIG. 3, it will be shown that the bandpass filter design shown therein is comprised of two inductive elements, namely, coil 84 and coil 46. Coil 84, much in the same way as coil 41 in FIG. 2, is the coil which is juxtaposed to the one pole of the magnet 56 in sensor 70 shown in FIG. 5. It will be appreciated the the sensor shown in FIG. 4 and FIG. 5 are identical with the exception that FIG. 5 shows a coil 46 at the opposite end of the magnet 56 from coil 84. The purpose of this arrangement is to provide a bandpass filter 40A whose center bandpass frequency does not change with the temperature change of the front coil 84. In this way, a more accurate mass accumulation measurement of debris 58 can be achieved. The only change of the inductance of coil 84 will be due to metallic mass accumulation 58 on pole piece 57. Any temperature change of the wires comprising coil 84 shall be balanced out by the change in temperature of the back coil 46 which is identical in every dimension and composition to coil 84 used on the opposite end of the magnet 56 as shown. In this way, any change in the operating parameters of the coils 46 and 84, due to external operating conditions such as temperature, would change equally, thereby cancelling their effect in the bandpass filter shown in FIG. 3.

A possible change of operating parameter would be the change in temperature which would cause resistance change in the wire that comprises both coil 46 and 84. It is desirable that the output of integrated circuit amplifier 45 shown in FIG. 3, operating as a bandpass filter in the configuration shown, remain the same except for changed in the inductance of coil 84. Since the temperature change in the wire may cause an increase or decrease in resistance, it will be appreciated by those skilled in the art that the gain of an operational amplifier, such as those set forth in FIG. 2 and FIG. 3, would change the resistance of some of the peripheral components utilized in setting the gain of an operational amplifier and otherwise designing and choosing its set point. Since the gain of operational amplifier 45, acting as a bandpass filter in the present design, is controlled by the values R21, R22, R23 and R24 as shown, it will be appreciated that the present design in FIG. 3 would cause the gain of amplifier 45 to remain constant irrespective of the resistance change of the wiring coil 84 and 46, which essentially would serve to cancel out the affect of each other's resistance change due to temperature. It will be appreciated that, in the schematic shown in FIG. 3, R21 must equal the value of R22. Likewise, R23 must equal the value of R24 in the design of the circuit. The wire and other material used to manufacture coil 84 and 46 must be identical, so that their internal resistance is due to the resistance of the wire within each coil is identical. In the preferred embodiment, the copper alloy known as Coupron, having a resistance of 1 ohm per 20 foot is utilized with good results.

Although the present invention has been described with reference to the particular embodiments hereinsetforth, it is understood that the present disclosure has been made only by way of example and that numerous changes in the details of construction may be resorted to without departing from the spirit and scope of the invention. Thus, the scope of the invention should not be limited by the foregoing specification, but rather only by the scope of the claims appended hereto

What is claimed is:

1. Article for sensing ferrous contamination in a fluid comprising:
    (a) a generally cylindrical magnet;
    (b) a first electrical coil located co-axially on one end of said magnet, said coil having a hole lengthwise through its center;

(c) a pole piece of said magnet occupying the hole in said first coil and concentric with said magnet disposed at one end of the magnet, said pole piece of the magnet being available to accumulate ferrous contamination present in a fluid whereby any ferrous accumulation changes the induction of the coil;

(d) a second coil, indentical in composition and inductance to said first coil, the axis of the second coil being concentric to the axis of said magnet and located on the opposite end of the generally cylindrical magnet from the said first coil, the inductance of said second coil being unaffected by said ferrous accumulation;

(e) frequency generation means for generating a fixed, known frequency sine wave signal of a known amplitude;

(f) an electrical bandpass filter including means connecting said first and second coils as the frequency determinative element of the filter, both of said coils being equally affected by variations in external operating conditions, whereby changes in the outputs of said coils due to such variations cancel each other in said filter, the input of the filter being operatively connected to said frequency generation means;

(g) amplification means operatively connected to the output of said filter.

* * * * *